United States Patent [19]

Magnone

[11] Patent Number: 5,892,073
[45] Date of Patent: Apr. 6, 1999

[54] PROCESS FOR PREPARATION OF 13-CIS-RETINOIC ACID

[75] Inventor: Angelo Grato Magnone, Milan, Italy

[73] Assignee: Laboratori Mag S.p.A., Italy

[21] Appl. No.: 995,392

[22] Filed: Dec. 22, 1997

[30] Foreign Application Priority Data

Dec. 27, 1996 [IT] Italy .................................. MI96A2752

[51] Int. Cl.$^6$ ............................ C07C 51/353; C11C 3/14
[52] U.S. Cl. ...................... 554/125; 204/157.64
[58] Field of Search ........................ 554/125; 204/157.67

[56] References Cited

U.S. PATENT DOCUMENTS 4,556,518  12/1985  Lucci .
5,424,465   6/1995  John et al. ............................... 554/125

FOREIGN PATENT DOCUMENTS 0742204  11/1996  European Pat. Off. .
4313089  10/1994  Germany .

OTHER PUBLICATIONS

European Search Report, Sep. 4, 1997, Examiner Bonnevalle, E.

J. Chem. Soc. 1984 (1964); "Carotenoids and Related Compounds, Part XVIII.$^1$ Synthesis of Cis– and Di–Cis–Polyenes by Reactions of the Witting Type", by Gerald Pattenden and B.C.L. Weedon.

*Primary Examiner*—Gary Geist
*Assistant Examiner*—Deborah D Carr
*Attorney, Agent, or Firm*—Hedman, Gibson & Costigan, P.C.

[57] ABSTRACT

Photochemical isomerization of 11-cis-, 13-cis-retinoic acid to 13-cis-retinoic acid characterized in that it is performed in an aqueous solution of an alkaline salt of said 11-cis-, 13-cis-retinoic acid.

8 Claims, No Drawings

PROCESS FOR PREPARATION OF 13-CIS-RETINOIC ACID

SCOPE OF INVENTION

The present invention regards a process of photochemical isomerization of 11-cis-, 13-cis-retinoic acid to 13-cis-retinoic acid.

TECHNOLOGICAL BACKGROUND

The 13-cis-retinoic acid characterized by the following formula:

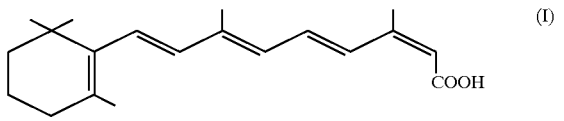
(I)

is an active principle that finds widespread practical application in various treatments and is used in particular for the treatment of acne. In "Carotenoids and Related Compounds. Part XVIII. Synthesis of cis and Di-cis-Polyenes by Reactions of Wittig Type", Paddenten G., Weedon B. C. L., J. Chem. Soc. (C) 1968, pages 1984–1997, a process is described for preparing this product, which comprises a Wittig condensation at ambient temperature in ethereal solvent in the presence of sodium methoxide of the halide of [3-methyl-5-(2,6,6-trimethyl-1-cyclohexene-1-yl-2,4-pentadienyl]-triphenyl-phosphonium of formula (II)

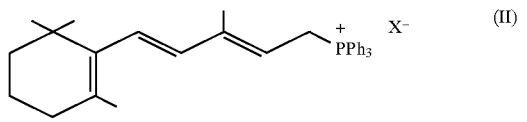
(II)

where X is a halogen atom, with 5-hydroxyl-4-methyl-2(5-H)-furanone of formula (III)

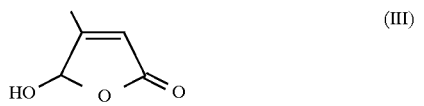
(III)

This process, however, presents the disadvantage that the desired product is obtained mixed with the following isomers: 11-cis-, 13-cis-retinoic acid of formula (IV)

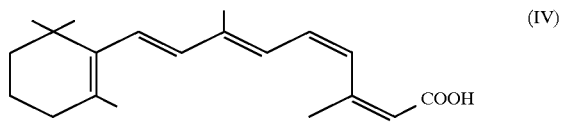
(IV)

and 11-trans-,13-trans-retinoic acid (i.e., the acid of vitamin A), of formula (V)

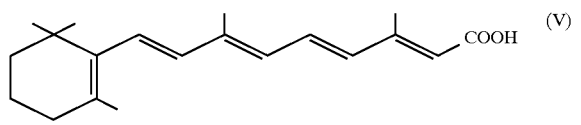
(V)

The product (I) obtained in a minority amount compared to the isomer (IV) and in amounts more or less comparable to those of the isomer (V), must then be separated from the mixture with conventional methods for silica chromatography by means of fractional crystallization, these being treatments which further reduce the yields.

The patent EP 0111325 describes a process for preparation of 13-cis-retinoic acid, characterized by the fact that the Wittig condensation between product (II) and product (III) occurs at low temperatures of between –10° C. and –50° C. in alcoholic solvent and in the presence of bases consisting of alkaline metal hydroxides, such as potassium hydroxide.

In this way, a conversion is obtained of over 90% calculated with respect to the starting product (III); the reaction product consists of a mixture containing between 10% and 30% of isomer (I) and between 70% and 90% of isomer (IV). The mixture as such, or the isomer (IV) alone previously separated from the aforesaid mixture, undergoes a process of isomerization in the presence of rhodium-based or palladium-based catalysts that are able to convert the product (IV) into 13-cis-retinoic acid.

Although this process enables 13-cis-retinoic acid to be obtained in higher yields than those obtained with the process described in the previous document, it presents the drawback that the isomerization of 11-cis,13-cis-retinoic acid of formula (IV) occurs with catalysts containing transition metals, such as rhodium and palladium, that are extremely costly. In addition, it is very difficult to recover the 13-cis-retinoic acid from the raw reaction product containing the aforesaid catalysts with the chemical purity required by current manufacturing standards.

The patent DE 4313089 describes a process to prepare 13-cis-retinoic acid in which the reaction between 5-hydroxyl-4-methyl-furanone (III) with the salt of [3-methyl-5-(2,6,6-trimethy-1-1-cyclohexene-1-yl)-2,4-pentadienyltriaryl-phosphonium (II) is carried out in the presence of lithium hydroxide and dimethylformamide at temperatures of between 10° C. and –9° C. to obtain a mixture of lithium salts of 13-cis-retinoic acid and of 11-cis, 13-cis-retinoic acid, which are subsequently solubilized in water and converted into their respective acids by addition of sulphuric acid. The residue is recovered which consists of a mixture of the two acids and which is then solubilized in alcoholic solvent, and subsequently undergoes photochemical isomerization to obtain 13-cis-retinoic acid.

Even though this method represents a considerable improvement over the previous process in that the isomerization process does not require the use of the aforesaid catalysts, it presents a series of drawbacks in that photochemical isomerization must be carried out on the mixture of the isomers coming from the Wittig condensation, previously isolated from the reaction solvents. The aforesaid retinoic acids are moreover not very soluble in the reaction solvents compatible with photochemical isomerization. In fact, photochemical isomerization must be carried out only on solutions of the aforesaid solvents containing the mixture of acids in concentrations of less than 10%. This type of photochemical isomerization, if applied on an industrial scale, requires considerable quantities of solvents, which is disadvantageous from the economic standpoint of the process, as well as from the standpoint of the safety of operators carrying out this process. In addition to this, the use of organic solvent for this type of reaction entails particular equipment and costly fire-prevention and explosion-prevention systems. Furthermore, the mixture of acids is rather unstable in organic solvents.

For these reasons, the need has been felt for having available a process for the production of 13-cis-retinoic acid that should not present the drawbacks of the processes known in the present state of the art.

SUMMARY

The applicant has now unexpectedly found a process of conversion of 11-cis,13-cis-retinoic acid of formula (IV) to 13-cis-retinoic acid by means of photochemical isomerization in the presence of photo-activators at ambient temperature, characterized in that it is carried out on an aqueous solution of the alkaline salt of said 11-cis, 13-cis-retinoic acid (IV).

The isomerization process that is the subject of the present invention presents in particular the following advantages:

i) the alkaline salts of 11-cis, 13-cis-retinoic acid in aqueous solution are much more stable than the corresponding undissociated acid;

ii) the isomerization reaction carried out on the alkaline salt and in aqueous solution is faster than that carried out on undissociated acid and in organic solvent;

iii) the use of aqueous solutions in the photochemical isomerization reaction, instead of the organic solvent envisaged in the known photochemical isomerization reactions, greatly reduces the risks for operators working on these systems;

iv) the scale up is therefore possible in so far as the risks of fire or explosion involved in the use of organic solvents are reduced;

v) the use of water instead of organic solvents represents a notable economic saving and moreover renders the disposal of the process waters less burdensome;

vi) isomerization in aqueous solution may be carried out on a solution with a concentration of up to 30%.

DETAILED DESCRIPTION OF INVENTION

The irradiation used to carry out photochemical isomerization of 11-cis, 13-cis-retinoic acid is visible light with a wavelength of 330 nm; consequently, at radiations with wavelengths decidedly shorter than those necessary for carrying out photochemical isomerization in organic solvent on the corresponding 11-cis, 13-cis-retinoic acid, which is 353 nm. Even though as photo-activator in the present photochemical isomerization reaction it is possible to use bengal rose, diphenyl disulphide, cercosporin and chlorophyll, the photo-activator that yields the best results is bengal rose.

The photochemical isomerization process of the present invention is preferably carried out on potassium salt or sodium salt of 11-cis, 13-cis-retinoic acid or on the mixture of the potassium salts of 13-cis-retinoic acid (I), 11-cis,13-cis-retinoic acid (IV), and 11-trans-, 13-trans-retinoic acid, in particular when this type of reaction is used to enrich, in the desired product, the mixture of the aforesaid acids coming from the Wittig condensation between the above-mentioned phosphonium salt (II) and the product (III).

The Wittig condensation is preferably conducted following different operating procedures, for example as described in "Carotenoids and Related Compounds. Part XVIII. Synthesis of cis and Di-cis-Polyenes by Reactions of Wittig Type", Paddenten G., Weedon B. C. L., J. Chem. Soc. (C) 1968, pages 1984–1997, at ambient temperature in ethereal solvent in the presence of sodium methoxide, or, as described in the patent EP 115325, in alcoholic solvent, preferably ethanol, at temperatures of between –10° C. and –50° C. in the presence of an alkaline hydroxide, preferably potassium hydroxide.

The salts coming from the Wittig condensation may directly undergo photochemical isomerization with the process that is the subject of the present invention, or undergo a series of purification treatments that involve, among other things, also an intermediate acidification and extraction in organic solvents. In any case, once these acids have been purified, before undergoing photochemical isomerization with the process according to the invention, they are previously reconverted into alkaline salts for treatment with an aqueous solution of an alkaline hydroxide.

The reaction mixture coming from the photochemical isomerization process that is the subject of the present invention is subsequently acidified with a strong mineral acid, preferably sulphuric acid, and the desired product may be recovered using different operating techniques.

For example, it may be recovered by mere filtration of the product that has precipitated from the aqueous solution. Alternatively, for example, chloroform may be added to the aqueous mixture coming from the isomerization process, and the mixture can then be acidified. In this case, the aqueous phase is removed, and the solvent is removed from the appropriately washed organic phase.

Finally, the product may be recovered as follows: the aqueous solution coming from the acidified photochemical isomerization may be extracted with ethyl acetate/hexane (4:1), the organic phase containing the desired product is subsequently washed with methanol/water (3:1), dehydrated, and evaporated. In any case, the recovery of the desired product after acidification and mere filtration of the product precipitated from the aqueous solution is decidedly the method to be preferred. The product obtained with the synthetic process that is the subject of the present invention may, if required, can be crystallized, and the best results are obtained when ethyl acetate is used as the crystallization solvent.

The following examples are given as possible illustrations, which, however, do not limit the possibilities, of the isomerization process according to the present invention.

EXAMPLE 1

Preparation of the isomer mixture of the potassium salts of the 11-cis, 13-cis-retinoic acid, 13-cis-retinoic acid and 11-trans-, 13-trans-retinoic acid 75 g 3-methyl-5-(2,6,6-trimethyl-1-cyclohexene-1-yl-2, 4-pentadiene and 103 g triphenylphosphine hydrochloride are dissolved in 600 ml ethanol to obtain the product (II). After overnight stirring, 76 g of (III) and 90 g of KOH are added, and after 1 hour the obtained mixture is diluted with 450 g of water, and finally the organic solvent is evaporated.

The aqueous phase contains retinoic acids in the following proportions (by HPLC analysis): 13-cis-retinoic acid 21.93%; 11-cis, 13-cis-retinoic acid 67.4%; and 11-trans-, 13-trans-retinoic acid 7.26%. The weight of the aqueous phase is 800 g.

EXAMPLE 2

Photochemical isomerization conducted directly on the aqueous phase coming from the reaction described in Example 1

250 g of the mixture obtained above are put into a glass reactor and irradiated with an 8-Watt Hitachi® lamp F8T5/CW, in the presence of 1 mg of bengal rose. After 2 hours, HPLC reveals the following composition: 13-cis-retinoic acid, 66,22%; 11-cis, 13-cis-retinoic acid, 0.6%; and 11-trans-,13-trans-retinoic acid, 33.19%.

The reaction mixture obtained above is acidified and extracted three times with a mixture of ethyl acetate/hexane (4:1). The organic phase is in turn washed with methanol/water (3:1). The organic phase is dehydrated, and the solvent is evaporated. The residue consists of retinoic acids in which the desired 13-cis-retinoic acid accounts for 95%. By ethyl acetate crystallization, 15 g of the desired product are obtained with 99% purity, 50% yield on the original 3-methyl-5-(2,6,6-trimethyl-1-cyclohexene-1-yl)-2,4-pentadiene.

EXAMPLE 3

Photochemical isomerization on the mixture coming from Example 1 previously acidified and subsequently resalified 100 g of the aqueous phase obtained at the end of condensation, as described in Example 1, are acidified, when cold, with diluted sulphuric acid, and the mixture is extracted three times with 80 ml of ethyl ether. The re-united organic phase is washed twice with 50 ml of water/methanol (3:1), and then with water alone. The residue obtained by evaporation of the ethereal organic phase previously dehydrated weighs 11 g and has the same composition (upon HPLC analysis) of retinoic acids as that reported in Example 1, as regards the corresponding salts. These 11 g of product are dissolved in 20 ml water containing 2.4 g KOH. To this, 0.1 mg bengal rose are added and the products is then subjected to light irradiation for 2 hours to obtain a mixture which, upon HPLC analysis, is found to have the following composition: 13-cis-retinoic acid, 67.11%; 11-cis, 13-cis-retinoic acid, 0.7%; and 11-trans-, 13-trans-retinoic acid product 32.3%.

The recovery of the desired 13-cis-retinoic acid is carried out by acidifying the mixture, when cold, with diluted sulphuric acid and collecting the precipitate by filtration.

The latter product is washed with water directly on the filter, and finally dried and crystallized using ethyl acetate to give 5.8 g of the product with 99% purity. Alternatively, chloroform is added to the isomerization mixture, and the mixture is subsequently acidified whilst it is kept stirred. The organic phase is next washed with water, dehydrated and evaporated to yield a residue which, after crystallization by hexane, gives 6.2 g of 13-cis-retinoic acid, and is subsequently recrystallized by ethyl acetate to yield 5.5 g of the desired product with 99% purity.

COMPARISON EXAMPLE

For the purposes of comparison, the same quantity of isomer mixture (11 g) dissolved in 130 ml of ethanol with the addition of 0.1 mg of bengal rose must be irradiated with the same device for 4 hours to obtain the same distribution of the products as observed operating on potassium salts in concentrated aqueous phase as described above.

EXAMPLE 4

Preparation of a mixture of retinoic acids (I), (IV) and (V)

Into 300 ml of methanol 50 g of 3-methyl-5-(2,6,6-trimethyl-1-cyclohexene-1-yl-2,4-pentadiene and 80 g of triphenylphosphine bromhydrate are put. After overnight stirring of the mixture, the solvent is evaporated and the raw reaction product is rediluted with 500 ml anhydrous ether. The reaction mixture is then treated with 50 ml of sodium methylate prepared from 6.9 g of metallic sodium. After 20 minutes, 8 g (III) are added in 10 ml ether. After 1 hour, the mixture is diluted with 200 ml hexane and extracted three times with 100 ml a methanol/water (1:1) mixture. From the acidified methanolic waters, the mixture of retinoic acids is extracted three times with 100 ml ether. The etheral phase is subsequently washed with a mixture of water/methanol (3:1), and then with water and sodium chloride. The organic phase is dehydrated, and the solvent is evaporated. Then 33 g of a mixture are obtained, which, upon HPLC analysis, is found to consist of:

13-cis-retinoic acid (I) 23%;
11-cis, 13-cis-retinoic acid (IV) 64%;
11-trans-, 13-trans-retinoic acid (V) 13%.

EXAMPLE 5

Photochemical isomerization

The 33 g of the mixture of retinoic acids (I), (IV) and (V) obtained in the previous example are dissolved in 60 ml of water containing 9.2 g of KOH. To this 0.1 mg bengal rose are added, and the mixture is subjected to light irradiation for 2 hours to obtain a mixture which, upon HPLC analysis, presents the following composition: 13-cis-retinoic acid, 65.7%; 11-cis, 13-cis-retinoic acid 24.2%; and 11-trans-, 13-trans-retinoic acid 10.1%.

The recovery of the desired 13-cis-retinoic acid is obtained by acidifying the mixture, when cold, with diluted sulphuric acid and collecting the precipitate by filtration.

The latter is washed with water directly on the filter, and finally dried and crystallized by ethyl acetate to give a product with 99% purity and 53% yield.

I claim:

1. Process of conversion of 11-cis, 13-cis-retinoic acid of formula (IV).

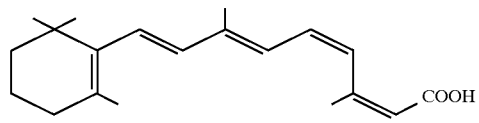

to 13-cis-retinoic acid (I)

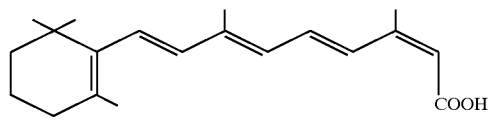

by photochemical isomerization at ambient temperature in the presence of photo-activators, characterized in that the process is carried out on an aqueous solution of the alkaline salt of said 11-cis, 13-cis-retinoic acid (IV).

2. Process according to claim 1, wherein the irradiation used to carry out the photochemical isomerization of 11-cis, 13-cis-retinoic acid into 13-cis-retinoic acid is visible light with a wavelength of 330 nm.

3. Process according to claim 1, wherein the photo-activator is bengal rose.

4. Process according to claim 1, being carried out on potassium or sodium salt of 11-cis, 13-cis-retinoic acid.

5. Process according to claim 1, wherein to enrich the product (I) mixtures are used containing also the products (I) and (V) coming from the Wittig condensation between the halide of [3-methyl-5-(2,6,6-trimethyl-1-cyclohexene-1-yl-2,4-pentadienyl]-triphenyl-phosphonium of formula (II)

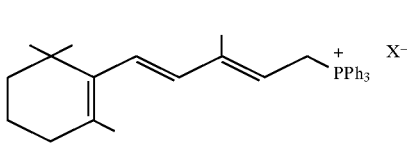

in which X is a halogen, and 5-hydroxy-4-methyl-2(5-H)-furanone of formula (III)

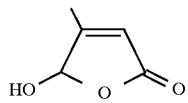

carried out at ambient temperature in ethereal solvent and in the presence of sodium methoxide.

6. Process according to claim 1, being carried out on mixtures containing prevalently the isomers (IV) and (I) coming from the Wittig condensation between the halide of [3-methyl-5-(2,6,6-trimethyl-1-cyclohexene-1-yl-2,4-pentadienyl]-triphenyl-phosphonium of formula (II)

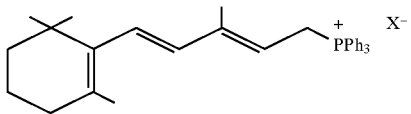

in which X is a halogen, and 5-hydroxy-4-methyl-2(5-H)-furanone of formula (III)

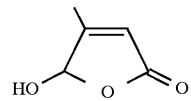

carried out at temperatures between −10° and −50° C. in alcoholic solvent and in the presence of bases consisting of hydroxides of alkaline metals.

7. Process according to claim 1, wherein the reaction mixture coming from photochemical isomerization is subsequently acidified with a strong mineral acid, and the desired product is recovered by filtration of the product precipitated from the aqueous solution.

8. Process according to claim 7, wherein the recovered product is crystallized by ethyl acetate.

* * * * *